US008002849B2

(12) United States Patent
Prem et al.

(10) Patent No.: US 8,002,849 B2
(45) Date of Patent: Aug. 23, 2011

(54) COMPOSITION KIT, AND METHOD FOR COLORING THE HAIR UTILIZING SACCHARIDE-SILOXANE COPOLYMERS

(75) Inventors: Pradmaja Prem, Saddle Brook, NJ (US); Aziza Suleiman, Paterson, NJ (US); Marie Huynh, Monmouth Junction, NJ (US); Praddhyumana Patel, Spotswood, NJ (US); Frederic Cervantes, Westfield, NJ (US)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/746,550

(22) PCT Filed: Dec. 18, 2008

(86) PCT No.: PCT/US2008/087307
§ 371 (c)(1),
(2), (4) Date: Jun. 7, 2010

(87) PCT Pub. No.: WO2009/079610
PCT Pub. Date: Jun. 25, 2009

(65) Prior Publication Data
US 2010/0242982 A1    Sep. 30, 2010

Related U.S. Application Data

(60) Provisional application No. 61/014,989, filed on Dec. 19, 2007.

(51) Int. Cl.
*A61Q 5/10* (2006.01)
(52) U.S. Cl. ............. 8/405; 8/435; 8/552; 8/559; 8/581; 8/609; 132/202; 132/208
(58) Field of Classification Search ............... 8/405, 435, 8/552, 559, 581, 609; 132/202, 208
See application file for complete search history.

(56) References Cited

U.S. PATENT DOCUMENTS

| 4,898,595 | A | 2/1990 | Fridd et al. |
|---|---|---|---|
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,747,016 | A | 5/1998 | Yui et al. |
| 5,766,576 | A | 6/1998 | Lowe et al. |
| 6,099,592 | A | 8/2000 | Vidal et al. |
| 6,326,011 | B1 | 12/2001 | Miyazawa et al. |
| 6,372,203 | B1 | 4/2002 | Allwohn et al. |
| 6,589,517 | B1 | 7/2003 | McKelvey et al. |
| 6,627,183 | B1 | 9/2003 | Young et al. |
| 2002/0031484 | A1 * | 3/2002 | Douin et al. ............ 424/70.1 |
| 2002/0197226 | A1 | 12/2002 | Giroud et al. |
| 2005/0002891 | A1 * | 1/2005 | Aubrun-Sonneville et al. ....... 424/70.17 |
| 2006/0064824 | A1 | 3/2006 | Godfrey |
| 2010/0239514 | A1 | 9/2010 | Prem et al. |

FOREIGN PATENT DOCUMENTS

| DE | 3843892 | 6/1990 |
|---|---|---|
| DE | 4133957 | 4/1993 |
| DE | 195 43 988 | 5/1997 |
| FR | 2 733 749 | 11/1996 |
| GB | 1026978 | 4/1966 |
| GB | 1153196 | 5/1969 |
| WO | WO 94/08969 | 4/1994 |
| WO | WO 94/08970 | 4/1994 |
| WO | WO 2006/127883 A2 * | 11/2006 |

OTHER PUBLICATIONS

John A. Wenninger, G.N. McEwen, Jr., International Cosmetic Ingredient Dictionary and Handbook, 11th Edition, vol. 3, published by The Cosmetic, Toiletry and Fragrance Association Inc. (CTFA), 1101 17th Street, N.W., Suite 300, Washington, DC, USA, (2006).
International Preliminary Report on Patentability dated Jul. 1, 2010 in corresponding International Application No. PCT/US2008/087307.
International Search Report and Written Opinion of the International Searching Authority dated Feb. 6, 2009 in corresponding International Application No. PCT/US2008/087307.
Kirk-Othmer, Encyclopedia of Chemical Technology, 4th Edition, vol. 23, John Wiley and Sons, New York, (1997).

* cited by examiner

*Primary Examiner* — Eisa Elhilo
(74) *Attorney, Agent, or Firm* — Maria Luisa Balasta; Steven Trzaska

(57) ABSTRACT

The present invention relates to a method of coloring hair, comprising the steps of applying onto the hair a pre-treatment composition containing at least one saccharide-siloxane copolymer to form pre-treated hair, optionally, at least one emulsifier, optionally, at least one viscosity-modifying agent, and a cosmetically acceptable medium; applying a permanent hair coloring composition onto the pre-treated hair to form colored hair, rinsing the colored hair, optionally, applying a post-treatment composition to the hair, and optionally, rinsing the colored hair.

17 Claims, No Drawings

COMPOSITION KIT, AND METHOD FOR COLORING THE HAIR UTILIZING SACCHARIDE-SILOXANE COPOLYMERS

STATEMENT OF RELATED APPLICATIONS

This application is a national phase of PCT/US08/87307, filed on Dec. 18, 2008 which claims priority to U.S. Provisional Application No. 61/014,989, filed Dec. 19, 2007, the entire contents of all are hereby incorporated by reference.

FIELD OF THE INVENTION

The present invention relates to a composition, kit and method of coloring hair which accelerates the hair dyeing process, provides greater color deposition thereby yielding increased color intensity, color vibrancy, and color protection to artificially colored hair, with reduced hair surface damage.

BACKGROUND OF THE INVENTION

Hair is composed of keratinous fibers and is inclusive of head hair, eyebrows, eyelashes, mustache, beard, and other types of body hair. Hair is commonly dyed with various coloring agents. Currently marketed permanent hair coloring products recommend a minimum coloring time of 30 minutes in order to obtain the desired coloring effect. A long coloring time is known to be damaging to the hair, due to prolonged exposure to oxidizing agents and alkalizing agents. There is thus a need for reducing the coloring time when artificially coloring the hair without compromising the intensity and vibrancy of the resulting deposited hair color.

It has been surprisingly discovered that by pre-treating the hair with a cosmetic composition containing at least one saccharide-siloxane copolymer before coloring the hair, the hair coloring process is achieved in less time, while providing increased color intensity, color vibrancy, and color protection to artificially colored hair, with reduced hair surface damage generally attributed to the artificial coloring of hair.

SUMMARY OF THE INVENTION

The present invention is directed to a method of coloring the hair, comprising the steps of:
a) applying onto the hair a pre-treatment composition containing:
 (i) at least one saccharide-siloxane copolymer to form pre-treated hair;
 (ii) optionally, at least one emulsifier;
 (iii) optionally, at least one viscosity-modifying agent; and
 (iv) a cosmetically acceptable medium;
b) applying a permanent hair coloring composition onto the pre-treated hair to form colored hair;
c) rinsing the colored hair;
d) optionally, applying a post-treatment composition to the hair, and
e) optionally, rinsing the colored hair.

The present invention is also directed to a hair coloring kit, comprising a multi-unit receptacle having:
a) at least one unit containing a pre-treatment composition comprising at least one saccharide-siloxane copolymer;
b) at least one unit containing a coloring base composition comprising at least one hair dye material;
c) at least one unit containing a developer composition comprising at least one oxidizing agent; and
d) optionally, at least one unit containing at least one post-treatment composition.

The present invention is also directed to a hair cosmetic composition containing:
a) at least one saccharide-siloxane copolymer to form pre-treated hair;
b) optionally, at least one emulsifier;
c) optionally, at least one viscosity-modifying agent; and
d) a cosmetically acceptable medium.

The present invention is also directed to a method of imparting color vibrancy onto artificially colored hair comprising applying onto the hair a cosmetic composition containing:
a) at least one saccharide-siloxane copolymer;
b) optionally, at least one emulsifier; and
c) optionally, at least one viscosity-modifying agent; and
d) a cosmetically acceptable medium.

DETAILED DESCRIPTION OF THE INVENTION

Other than in the operating examples, or where otherwise indicated, all numbers expressing quantities of ingredients and/or reaction conditions are to be understood as being modified in all instances by the term "about".

As used herein, the expression "at least one" means one or more and thus includes individual components as well as mixtures/combinations.

"Cosmetically acceptable" means that the item in question is compatible with any keratin material. For example, "cosmetically acceptable medium" means a medium that is compatible with any keratin material.

"Keratin material" includes, for example, skin, hair, nails, eyelashes, eyelids, eyebrows, lips and any other area of body or facial skin.

It has now been surprisingly and unexpectedly found that the use of a pre-treatment composition comprising at least one saccharide-siloxane copolymer results in accelerating the rate of color formation when artificially coloring the hair, while also providing enhanced color intensity, color vibrancy, and reduced hair surface damage.

A. Saccharide-Siloxane Copolymer

The pre-treatment composition contains at least one saccharide-siloxane copolymer. Various synthetic routes to suitable saccharide-siloxane copolymers are well known in the art and may be employed. One of ordinary skill in the art will appreciate that suitable saccharide-siloxanes may be formed from a variety of synthetic means and that the saccharide may be covalently linked to the siloxane through a variety of linking bonds described below.

The saccharide-siloxane copolymer has the following structure:

Y-X-S-X-Y

Wherein Y is a hydroxyl-functional substituted or unsubstituted saccharide bonded to the organopolysiloxane group, S, through linking group, X. According to one aspect of the present invention, the hydroxyl-functional saccharide comprises an aldonic acid or an oligoaldonic acid. In a more specific embodiment the aldonic acid or the oligoaldonic acid comprises a lactone. Two exemplary lactones include gluconolactone and lactobionolactone.

Other hydroxyl-functional saccharides which may be used include a) monosaccharide units such as glucopyranose (glucose), mannose, allose, altrose, galactose, idose, talose, gulose, ribose, arabinose, xylose, fructose, fucose, N-acetylglucosamine, N-acetylgalactosamine, sialic acid, and esters of the preceding, and b) polysaccharide units such as cellulose, amulose, and their esters. Gluconolactone is preferred among the preceding as the hydroxyl-functional saccharide.

The organopolysiloxane group, S, along with linking group X, can be specifically exemplified as:

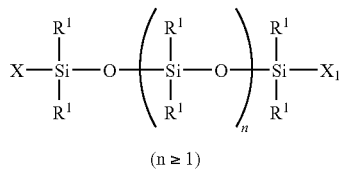

(n ≥ 1)

Wherein $R^1$ is a $C_1$ to $C_{10}$ substituted or unsubstituted linear or branched alkyl or aryl groups. The alkyl can be exemplified: by methyl, ethyl, propyl, butyl, pentyl, isopropyl, isobutyl, cyclopentyl, and cyclohexyl, while the aryl can be exemplified by phenyl and naphthyl. Methyl is preferred among the preceding for $R^1$.

The linking group X may be chosen from an alkyl, amide, amino, urethane, urea, ester, ether, thioether, epoxide, or acetal functional linking group. A secondary amino is preferred among the preceding as the linking group.

An example of a suitable saccharide-siloxane copolymer is Gluconamidoethylaminopropyl Silicone sold by Dow Corning under the product name CE-8810 SUGAR SILICONE EMULSION.

The saccharide-siloxane copolymer is typically present in the inventive composition in an amount of from about 0.01% to about 50% by weight, preferably from about 1% to about 20% by weight, and more preferably from about 1% to about 10% by weight, based on the total weight of the composition.

In other embodiments of the present invention, the saccharide-siloxane copolymer may be present in the inventive composition in an amount of up to about 60.0% by weight, based on the total weight of the composition.

B. Viscosity-Modifying Agent

The pre-treatment composition may further comprise at least one viscosity-modifying agent. Suitable viscosity-modifying agents may be chosen from fatty acid amides, for example, coconut monoethanolamide, coconut diethanolamide, and oxyethylenated carboxylic acid alkyl ether monoethanolamide; cellulose-based thickeners, such as hydroxymethylcellulose, hydroxyethylcellulose, hydroxypropylcellulose, and hydroxypropylmethylcellulose; guar gum and its derivatives, for instance, the hydroxypropyl guar gum sold under the name JAGUAR HP105 by the company Rhodia; gums of microbial origin, for example, xanthan gum and scleroglucan gum); and nonionic associative polymers.

Non-limiting examples of nonionic associative polymers may include:

(1) celluloses modified with groups comprising at least one fatty chain, for example:

hydroxyethylcelluloses modified with groups comprising at least one fatty chain, such as alkyl, arylalkyl, and alkylaryl groups, and mixtures thereof, wherein the alkyl groups may be $C_8$-$C_{22}$ alkyl groups, for instance, the product Natrosol Plus Grade 330 CS® ($C_{1-6}$ alkyls) sold by the company Aqualon, the product Bermocoll EHM 100® sold by the company Berol Nobel, the product Methocel (hydroxylpropylcellulose) sold from Dow/Amerchol, the product Klucel (hydroxylpropryl methylcellulose) sold from Hercules, and, celluloses modified with alkylphenyl polyalkylene glycol ether groups, such as the product Amercell Polymer HM-1500® (nonylphenyl polyethylene glycol (15) ether) sold by the company Amerchol;

(2) hydroxypropyl guars modified with groups comprising at least one fatty chain, such as the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhone-Poulenc;

(3) copolymers of vinylpyrrolidone and of fatty-chain hydrophobic monomers; for example:

the products Antaron V216® or Ganex V216® (vinylpyrrolidone/hexadecene copolymer) sold by the company I.S.P; and the products Antaron V220® or Ganex V220® (vinylpyrrolidone/eicosene copolymer) sold by the company I.S.P;

(4) copolymers of $C_1$-$C_6$ alkyl methacrylates or acrylates and of amphiphilic monomers comprising at least one fatty chain, for example, the oxyethylenated methyl acrylate/stearyl acrylate copolymer sold by the company Goldschmidt under the name Antil 208®;

(5) copolymers of hydrophilic methacrylates or acrylates and of hydrophobic monomers comprising at least one fatty chain, for example, polyethylene glycol methacrylate/lauryl methacrylate copolymer.

(6) polyurethane polyethers comprising in their chain both hydrophilic blocks, for example, polyoxyethylenated blocks, and hydrophobic blocks, which may be aliphatic sequences alone and/or cycloaliphatic and/or aromatic sequences. Examples of such polyurethane polyethers include those sold by Rohm & Haas under the names Aculyn 44® and Aculyn 46®. Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%). Aculyn 44® is a polycondensate of polyethylene glycol containing 150 or 180 mol of ethylene oxide, of decyl alcohol and of methylenebis(4-cyclohexyl-isocyanate) (SMDI), at 35% by weight in a mixture of propylene glycol (39%) and water (26%);

(7) polymers with an aminoplast ether skeleton containing at least one fatty chain, such as the Pure Thix® compounds sold by the company Sud-Chemie.

Suitable viscosity-modifying agents for this invention may be chosen from cellulose-based thickeners, such as hydroxypropylcellulose, or acrylate-based polymers such as OPTA SENSE RMA52, manufactured by Croda. The viscosity-modifying agent(s) may be present in the composition in an amount of from about 0.2% to about 20.0% by weight, preferably from about 0.2% to about 10.0% by weight, and more preferably from about 0.2% to about 5.0% by weight, based on the total weight of the composition.

C. Emulsifier

The pre-treatment composition may further comprise at least one emulsifier. Non-limiting examples of emulsifiers may include esters of polyols and of a fatty acid having an alkyl chain containing from 12 to 22 carbon atoms, such as esters of fatty acid and of glycerol, of glucose or of sorbitol; oxyethylenated derivatives of esters of polyols and of a fatty acid having an alkyl chain containing from 12 to 22 carbon atoms, which derivatives contain from 1 to 50 oxyethylene groups, such as a complex of triisostearin (triester of glycerol and of isostearic acid) and of PEG-6; ethers of polyethylene glycol and of a fatty alcohol having an alkyl chain containing from 12 to 22 carbon atoms, which ethers contain from 1 to 50 oxyethylene groups, such as oleyl ethers and in particular oleth-25 (25 oxyethylene groups), and their mixtures.

Also included are polyol fatty esters and fatty ethers with a branched or unsaturated chain containing from 12 to 22 carbon atoms and, in particular, sorbitan monoisostearate, such as the product sold under the name "Arlacel 987" by the company ICI, sorbitan mono/dioleate, such as the product sold under the name "Arlacel 83" by the company ICI, the complex of triisostearin and of PEG-6, such as the product sold under the name "Labrafil isostearic" by the company Gattefossé, decaglyceryl pentaisostearate, such as the product sold under the name "Nikkol Decaglyn 5-IS" by the company Nikko Chemical, or methyl glucose dioleate, such as the product sold under the name "Isolan DO" by the company Goldschmidt.

Other examples include esters of polyethylene glycol and of a fatty acid having an alkyl chain containing from 12 to 22 carbon atoms, which esters contain from 5 to 100 and preferably from 20 to 60 oxyethylene groups, such as PEG-40 stearate; ethers of polyethylene glycol and of a fatty alcohol having an alkyl chain containing from 12 to 22 carbon atoms, which ethers contain from 5 to 100 and preferably from 10 to oxyethylene groups, such as ceteareth-25 or ceteth-25; esters of sorbitan and of a fatty acid having an alkyl chain containing from 12 to 22 carbon atoms, which esters comprise from 0 to 100 and preferably from 4 to 25 oxyethylene groups, such as polysorbate 20, polysorbate 40 and polysorbate 60; esters of sugar and of a fatty acid having an alkyl chain containing from 12 to 22 carbon atoms, such as sucrose stearate; derivatives of polyethylene glycol and of esters of glycerol and of a fatty acid having an alkyl chain containing from 12 to 22 carbon atoms, such as PEG-8 caprylic/capric glycerides; polyethylene glycol ethers of esters of methyl glucose and of a fatty acid having an alkyl chain containing from 12 to 22 carbon atoms, such as PEG-20 methyl glucose sesquistearate; and their mixtures.

Suitable emulsifiers for this invention may be chosen from glyceryl esters and polyethylene glycol esters of stearic acid, such as glyceryl stearate and PEG-100 stearate. The emulsifier may be present in the composition in an amount of from about __0.50% to about 10% by weight, preferably from about 1.0% to about 10.0% by weight, and more preferably from about 2.0% to about 7.0% by weight, based on the total weight of the composition.

D. Cosmetically Acceptable Medium

The compositions of the present invention can be formulated into or with any cosmetically acceptable carrier or diluent. Examples of such carriers or diluents are water, alcohols, polyols, and oils such as, for example, hydrocarbon oils and silicone oils. The carrier or diluent is typically present in the composition in an amount of from about 50% to about 95% by weight, preferably from about 60% to about 95% by weight, and more preferably from about 70% to about 95% by weight, based on the total weight of the composition.

E. Permanent Coloring Composition

The permanent coloring composition to be used in the present invention can be chosen from any commercial or conventional oxidative coloring system containing a coloring base and a developer.

1) Coloring Base

The coloring base contains at least one hair dye material. Such hair dye materials may be chosen from primary intermediates and/or couplers. Suitable primary intermediates are well known for use in hair color, and include ortho or para substituted aminophenols or phenylenediamines, double bases, bis(phenyl)alkylene-diamines, heterocyclic bases, and the acid addition salts thereof. The couplers that may be used include those conventionally used in oxidation dye compositions, such as meta-aminophenols, meta-phenylenediamines, meta-diphenols, naphthols, mono- or polyhydroxylated naphthalene derivatives, and heterocyclic couplers, and the acid addition salts thereof.

2) Developer Composition

The developer composition to be used in the present invention contains at least one oxidizing agent. Suitable oxidizing agents may be chosen from hydrogen peroxide, urea peroxide, melamine peroxide, persulfates, perborates, percarbonates and salts thereof.

F. Optional Ingredients

The compositions of the present invention may further comprise one or more components known for use in hair care compositions. Examples of such components include surfactants that are suitable for use on the hair or the skin. Suitable surfactants include non-ionic surfactants, anionic surfactants, amphoteric surfactants, zwitterionic surfactants, or mixtures thereof. Surfactants useful in the invention include those described in Kirk-Othmer, Encyclopedia of Chemical Technology (4.sup.th Ed.), vol. 23, John Wiley and Sons, Inc., NY and in the C.T.F.A. International Cosmetic Ingredient Dictionary and Handbook, $11^{th}$ edition, vol. 3, (2006). The surfactant can be selected for its cleansing property, foaming property, lathering property, emulsifying property or other desirable property.

Other examples of optional ingredients include, but are not limited to, ultraviolet light filters, dyes, hair colorants, hair fixatives, hair waving agents, hair straightening agents, organic solvents or diluents, foam boosters, pH adjusting agents, conditioning agents, humectants, lipids, fragrances, preservatives, proteins, protein derivatives, amino acids, amino acid derivatives, skin active agents, suspending agents, sunscreens, thickeners, vitamins, ceramide, uv absorbers (e.g., benzophenone), botanicals, anti-oxidants, retinoid, anti-dandruff, anti hair-loss and viscosity adjusting agents. These and other cosmetic additives commonly used in hair care formulations are described in, for example, C.T.F.A. International Cosmetic Ingredient Dictionary and Handbook, $11^{th}$ edition, vol. 3, (2006).

These optional components may be present in the composition in an amount of from about 0.01% to about 10.0% by weight, preferably from about 0.01% to about 5.0% by weight, and more preferably from about 0.01% to about 2.0% by weight, based on the total weight of the composition.

The compositions according to the present invention can be used in aqueous and anhydrous systems.

The pre-treatment compositions of the present invention preferably have a pH ranging from about 4.0 to about 8.0.

The pre-treatment compositions according to the present invention can also be used various types of formulations such as creams, sprays, lotions, mousses, gels, and gel-creams.

In at least one preferred embodiment, the pre-treatment composition is in the form of a cream.

In another preferred embodiment, the pre-treatment composition is in the form of a spray.

In another preferred embodiment, the pre-treatment composition is in the form of a gel.

The pre-treatment compositions of the present invention are used by applying to the hair before the hair has been colored. The hair may be wet, dry or semi-dry. The pre-treatment compositions described herein can be applied to the hair by working, rubbing, spraying, massaging, or combing through the composition into the hair so that substantially all or some of the hair is contacted with the composition. In one embodiment where treatment for only a portion of the hair is needed, the inventive pre-treatment composition can be applied to the localized region as needed. The pre-treatment composition may also be delivered onto the hair by use of an applicator or device. It is also desirable to have a uniform application of the pre-treatment composition onto the hair.

As a result of achieving an accelerated rate of color formation, the contact time of conventional oxidizing agents and alkalizing agents with the hair is minimized, thus reducing the degree of surface damage to the hair.

The inventive pre-treatment composition is applied to the hair before coloration for a period of from about 30 seconds to about 20 minutes, preferably from about 1 to 15 minutes, preferably from about 1 to 10 minutes, and more preferably from about 3-7 minutes.

After applying the inventive pre-treatment composition to the hair, the hair is then artificially colored using any commercial or conventional oxidative hair coloring composition or product. The hair may be in contact with the hair coloring composition for a period of about 30 minutes, or less. The hair is then rinsed with water and shampooed and/or conditioned, if desired.

In one preferred embodiment of the present invention, one or more post-treatment compositions are applied to the hair and the hair can be rinsed again, if desired or as instructed.

The one or more post-treatment composition can be chosen from hair conditioning compositions, shampoos, leave-in hair treatments, rinse-off hair treatments, and styling products.

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, unless otherwise specified.

EXAMPLES

Example I

Rate of Color Formation and Enhanced Color Deposition, Intensity and Vibrancy

The pre-treatment compositions are presented below. Composition A is the inventive pre-treatment composition. Composition B is the control, representing a pre-treatment composition for hair color that is currently on the market.

|  | Composition A (Pre-treatment Cream Base I) | Composition B (Commercial Pre-treatment Composition) |
| --- | --- | --- |
| GLUCONAMIDOETHYLAMINOPROPYLSILICONE | 4.99985 |  |
| MYRISTYL ALCOHOL | 0.05 |  |
| STEARYL ALCOHOL | 2.55 |  |
| PHENOXYETHANOL | 0.10526 |  |
| CETYL ALCOHOL | 1.9 |  |
| CHLORHEXIDINE DIHYDROCHLORIDE | 0.05 |  |
| BUTYLOCTANOL | 0.5263 |  |
| IODOPROPYNYL BUTYLCARBAMATE | 0.005263 |  |
| ALCOHOL | 0.10526 |  |
| C11-15 PARETH-40 | 0.5263 |  |
| GLYCERYL STEARATE | 3.0 |  |
| PEG-100 STEARATE | 3.0 |  |
| METHYLPARABEN | 0.3 | 0.2 |
| Citric Acid | 0.0 | 0.08 |
| HYDROXYETHYLCELLULOSE |  | 0.04 |
| POLOXAMER 407 |  | 0.02 |
| CETYL ESTERS |  | 0.5 |
| BEHENTRIMONIUM CHLORIDE |  | 1.185 |
| CETEARYL ALCOHOL |  | 3.15 |
| ISOPROPYL ALCOHOL |  | 0.27 |
| 2-OLEAMIDO-1,3-OCTADECANEDIOL |  | 0.01 |
| ISOSTEARYL ALCOHOL |  | 0.025 |
| GLYCERYL LINOLEATE |  | 0.00672 |
| GLYCERYL OLEATE |  | 0.0031 |
| DIVINYLDIMETHICONE/DIMETHICONE COPOLYMER |  | 2.68 |
| LAURYL PEG/PPG-18/18 METHICONE |  | 0.175 |
| CHLORHEXIDINE DIGLUCONATE |  | 0.04 |
| DODECENE |  | 0.01875 |
| CETRIMONIUM CHLORIDE |  | 0.088 |
| Fragrance |  | 0.5 |
| QS DI water | 100 | 100 |
|  | pH = 6.0 | pH = 4.6 |

The ability of the inventive composition to accelerate the rate of color formation and to provide greater color deposition thereby yielding increased intensity and vibrancy to the hair was determined using the following protocol.

Swatches of 90% bleached hair were treated with either inventive pre-treatment composition A, the control composition B, or no pre-treatment composition. The swatches were then artificially colored using a composition containing a mixture of dye precursors resulting in various shades, including red and brown. Colorimetric measurements of the hair swatches were taken at various time points during the coloration process, including 10, 15, 20, 25, and 30 minutes.

The color intensity of each hair swatch was determined using the =LAB L*a*b* system using a Sphere Spectrophotometer SP60 Series. Six measurements were taken on each swatch, three on each side of the swatch, at the top, middle and bottom of each side.

The L coordinate represents the color intensity of the swatch being tested based on a dark to light scale, and therefore, the lower the L value, the darker the color deposit. The a coordinate represents the position between red and green. Negative values indicate green while positive values indicate red, and thus a higher value of a indicates a greater red deposit. The b coordinate represents the position between yellow and blue. Negative values indicate blue while positive values indicate yellow, and thus a higher value of b indicates a more yellow deposit. A difference of one unit between two L coordinates is believed to be visually perceivable by the naked eye. A difference of 0.5 units between two a coordinates or two b coordinates is believed to be visually perceivable by the naked eye.

The following results were obtained. The color formation using the inventive pre-treatment composition, a commercial pre-treatment composition and without the use of a pre-treatment composition was measured at different time points.

| Red Shade | | | | | |
|---|---|---|---|---|---|
| | Composition A | | Composition B | | No Pre-treatment |
| | Color measurement variable | | | | |
| Time | L | a | L | a | L | a |
| 10 minutes | 44 | 21.1 | 46 | 19.8 | 45 | 19.9 |
| 15 minutes | 39 | 23.1 | 42 | 21.9 | 40 | 22.0 |
| 20 minutes | 35 | 23.9 | 38 | 22.5 | 37 | 22.4 |
| 25 minutes | 34 | 23.8 | 36 | 23.1 | 35 | 22.9 |
| 30 minutes | 31 | 23.7 | 34 | 23.1 | 32 | 22.7 |

| Brown Shade | | | | | |
|---|---|---|---|---|---|
| | Composition A | | Composition B | | No Pre-treatment |
| | Color measurement variable | | | | |
| Time | L | b | L | b | L | b |
| 10 minutes | 38 | 8.2 | 41 | 7.9 | 39 | 8.0 |
| 15 minutes | 33 | 8.2 | 36 | 8.4 | 35 | 8.4 |
| 20 minutes | 32 | 8.6 | 32 | 8.5 | 32 | 8.2 |
| 25 minutes | 30 | 9.0 | 31 | 8.4 | 32 | 8.7 |
| 30 minutes | 28 | 9.2 | 30 | 8.4 | 29 | 8.2 |

The data above shows lower L values at various time points when comparing the swatch treated with inventive pre-treatment Composition A to the swatch treated with Composition B and no pre-treatment. This indicates more color was deposited on the swatch treated with inventive composition A at the various time points. For the swatches that were colored with a red shade, the data shows higher a values at various time points when comparing the swatch treated with inventive pre-treatment Composition A to the swatch treated with Composition B and no pre-treatment. This indicates a greater intensity of red on the swatch treated with inventive Composition A compared to the swatches pre-treated with Composition B or to the swatches with no pre-treatment at the various time points, again evidencing greater color deposit.

For the swatches that were colored with a brown shade, the data shows higher b values at the end of the coloring time when comparing the swatch treated with inventive pre-treatment Composition A to the swatch treated with Composition B and no pre-treatment. This indicates a greater intensity of brown on the swatch treated with inventive Composition A compared to the swatches pre-treated with Composition B or to the swatches with no pre-treatment at the end of the coloring time, again evidencing greater color deposit.

Furthermore, the differences in color intensity and vibrancy were also visually perceivable on the swatches. Swatches treated with inventive pre-treatment Composition A showed a greater color intensity and vibrancy based on visual observations as compared to the swatches treated with Composition B and the swatches that were not pre-treated with any composition.

Example II

Reduced Rate of Color Formation—Effect of Pre-Treatment Compared to No Pre-Treatment and to Commercial Pre-treatment Compositions at Shorter Time Points The rates of color formation were also observed on colored hair swatches pre-treated with the inventive composition containing 5% by weight of the saccharide-siloxane copolymer based on the total weight of the composition at shorter time points. At 1, 5, and 10 minutes after coloring hair, the hair swatches pre-treated with the inventive composition exhibited more intense and better color deposit compared to the hair swatches that were not pre-treated and to the hair swatches pre-treated with a commercial composition that did not contain the saccharide-siloxane copolymer.

Example III

Reduced Hair Surface Damage

Scanning Electron Microscopy (SEM) measurements were taken of the colored or dyed hair fibers after rinsing the fibers with water. Measurements were made using a Hitachi Tabletop Microscope (TM-1000) at a magnification of 20-10,000× at an accelerating voltage of 15 KV using a semiconductor BSE detection system. The SEM images of the untreated colored hair fibers showed a rougher cuticle surface wherein the cuticle edges were lifted up. The SEM images of the colored fibers which were pre-treated with the inventive composition showed a smoother and uniform hair cuticle surface compared to hair cuticle surface of the untreated hair fibers. Moreover, the hair cuticle surface of the colored hair fibers treated with the commercial pre-treatment composition appeared smoother than the cuticle surface of the untreated hair but it appeared rougher and more uneven compared to the cuticle surface of the hair fibers treated with the inventive pre-treatment composition.

Therefore, the use of the inventive pre-treatment composition reduced the surface damage to the hair which could be attributed to less contact time of common oxidizing agents and alkalizing agents with the hair as a result of an accelerated rate of color formation.

Example IV

Color Retention Data after Shampooing

The color retention after eight shampoo-wash cycles was compared for hair swatches pre-treated with the inventive compositions before coloring versus hair swatches that were not pre-treated before coloring. Each shampoo-wash cycle involved rinsing the hair, shampooing the hair with a conventional shampoo, rinsing the hair, and blow-drying the hair. This rinsing, shampooing, rinsing, and drying process consisted of one cycle. This shampoo-wash cycle was repeated for up to a total of eight cycles. Colorimetric measurements of the hair swatches were taken before the first shampoo cycle (after coloring the hair) and after the last shampoo cycle, using the general procedure described above. The results for hair colored with a red shade dye are presented as follows:

| After 8 Wash Cycles | ΔL | Δa | ΔE |
|---|---|---|---|
| CONTROL (No Pre- Treatment) | 4.7 | −1.95 | 5.1 |
| With Pre-Treatment (composition containing 5.0% by weight of the saccharide-siloxane copolymer based on the total weight of the composition) | 4.7 | −0.99 | 4.9 |

The ΔL or the difference between the L value after eight shampoo-wash cycles versus the initial L value right after coloring the hair swatches represents a change in the darkness or lightness of the color deposited or retained. The Δa value or the difference between the a value after eight shampoo-wash cycles versus the initial L value right after coloring the hair swatches represents a change in the amount of red color deposited or retained. The ΔE value represents the overall color change in the hair swatches after the eight shampoo-wash cycles. This is computed using the equation:

$$\Delta E = \sqrt{(L^*_1 - L^*_0)^2 + (a^*_1 - a^*_0)^2 + (b^*_1 - b^*_0)^2}$$

Where $L^*_0$, $a^*_0$, and $b^*_0$ are coordinates associated with initial color measurements right after coloring the hair and $L^*_1$, $a^*_1$, and $b^*_1$ are coordinates associated with the final color measurements right after eight shampoo-wash cycles.

Although there was no difference in the ΔL value, which indicates no change in the darkness of the color, the Δa value, which is related to the amount of red color retained after shampooing, was significantly lower for the pre-treated swatches compared to the Δa value measured for the control, untreated swatches. Furthermore, the ΔE value for the swatches pre-treated with the inventive composition is lower compared to the ΔE value for the untreated swatches. These results indicate significant color retention using the inventive pre-treatment composition.

Example V

Other Formulations Using the Inventive Composition

Pre-Treatment Cream Base II

| RM INCI NAME | % LEVEL |
|---|---|
| GLUCONAMIDOETHYLAMINOPROPYLSILICONE | 5 |
| STEARYL ALCOHOL | 2.55 |
| MYRISTYL ALCOHOL | 0.05 |
| PHENOXYETHANOL | 0.11 |
| POLYSORBATE 20 | 6 |
| CETYL ALCOHOL | 1.9 |
| CHLORHEXIDINE DIHYDROCHLORIDE | 0.05 |
| BUTYLOCTANOL | 0.53 |
| IODOPROPYNYL BUTYLCARBAMATE | 0.005 |
| ALCOHOL | 0.11 |
| C11-15 PARETH-40 | 0.53 |
| HYDROXYPROPYL CELLULOSE | 1.5 |
| METHYLPARABEN | 0.3 |
| Q.S. to Water | 100 |
| | pH 6.0 |

Water-Based Spray Formulation

| RM INCI NAME | % LEVEL |
|---|---|
| GLUCONAMIDOETHYLAMINOPROPYLSILICONE | 5 |
| PHENOXYETHANOL | 0.11 |
| GLUCOSE | 1 |
| METHYLISOTHIAZOLINE | 0.01 |
| BUTYLOCTANOL | 0.53 |
| PEG-40 HDROGENATED CASTOR OIL | 0.65 |
| ALCOHOL DENATURED | 5 |
| C11-15 PARETH-40 | 0.53 |
| FRAGRANCE | 0.2 |
| Q.S. to Water | 100 |
| | pH = 6.0 |

The invention claimed is:

1. A method of coloring hair, comprising the steps of:
   a) applying onto the hair a pre-treatment composition comprising:
      (i) at least one saccharide-siloxane copolymer;
      (ii) optionally, at least one emulsifier;
      (iii) optionally, at least one viscosity-modifying agent; and
      (iv) a cosmetically acceptable medium to form pre-treated hair;
   b) applying a permanent hair coloring composition onto the pre-treated hair to form colored hair;
   c) rinsing the colored hair;
   d) optionally, applying a post-treatment composition to the hair, and
   e) optionally, rinsing the colored hair.

2. The method of claim 1, wherein the at least one saccharide-siloxane copolymer is present in an amount from about 0.1% to about 60.0% by weight, based on the total weight of the composition.

3. The method of claim 1, wherein the at least one saccharide-siloxane copolymer is present in an amount from about 1.0% to about 20.0% by weight, based on the total weight of the composition.

4. The method of claim 1, wherein the at least one saccharide-siloxane copolymer is present in an amount from about 1.0% to about 10.0% by weight, based on the total weight of the composition.

5. The method of claim 1, wherein the at least one viscosity-modifying agent is chosen from fatty acid amides, cellulose-based thickeners, nonionic associative polymers and mixtures thereof.

6. The method of claim 1, wherein the at least one viscosity-modifying agent is present in an amount of from about 0.2% to about 20.0% by weight, based on the total weight of the composition.

7. The method of claim 1, wherein the at least one viscosity-modifying agent is present in an amount of from about 0.2% to about 5.0% by weight, based on the total weight of the composition.

8. The method of claim 1, wherein the at least one emulsifier is chosen from esters of polyols and of a fatty acid having an alkyl chain containing from 12 to 22 carbon atoms, oxyethylenated derivatives of esters of polyols and of a fatty acid having an alkyl chain containing from 12 to 22 carbon atoms, ethers of polyethylene glycol and of a fatty alcohol having an alkyl chain containing from 12 to 22 carbon atoms, polyol fatty esters and fatty ethers with a branched or unsaturated chain containing from 12 to 22 carbon atoms, esters of polyethylene glycol and of a fatty acid having an alkyl chain containing from 12 to 22 carbon atoms, esters of sorbitan and of a fatty acid having an alkyl chain containing from 12 to 22 carbon atoms, esters of sugar and of a fatty acid having an alkyl chain containing from 12 to 22 carbon atoms, and mixtures thereof.

9. The method of claim 1, wherein the at least one emulsifier is chosen from glyceryl esters, polyethylene glycol esters of stearic acid, and mixtures thereof.

10. The method of claim 1, wherein the at least one emulsifier is present in an amount of from about 0.50% to about 10% by weight, based on the total weight of the composition.

11. The method of claim 1, wherein the at least one emulsifier is present in an amount of from about 2.0% to about 7.0% by weight, based on the total weight of the composition.

12. The method of claim 1, wherein said pre-treatment composition has a pH ranging from about 4.0 to about 8.0.

13. The method of claim 1, wherein said pre-treatment composition is left on the hair for a period of from about 30 seconds to about 20 minutes before coloration.

14. The method of claim 1, wherein said pre-treatment composition is left on the hair for a period of from about 1 minute to about 10 minutes before coloration.

15. The method of claim 1, wherein the cosmetically acceptable medium is chosen from water, alcohols, polyols, and oils.

16. A hair coloring kit, comprising a multi-unit receptacle having:
   a) at least one unit containing a pre-treatment composition comprising at least one saccharide-siloxane copolymer;
   b) at least one unit containing a coloring base composition comprising at least one hair dye material;
   c) at least one unit containing a developer composition comprising at least one oxidizing agent; and
   d) optionally, at least one unit containing at least one post-treatment composition.

17. A method of imparting color vibrancy onto artificially colored hair comprising applying onto the hair a cosmetic composition containing:
   a) at least one saccharide-siloxane copolymer;
   b) optionally, at least one emulsifier; and
   c) optionally, at least one viscosity-modifying agent; and
   d) a cosmetically acceptable medium,
   wherein the cosmetic composition is applied onto hair before or after coloring the hair.

* * * * *